(12) United States Patent
Parrish

(10) Patent No.: US 8,034,744 B2
(45) Date of Patent: Oct. 11, 2011

(54) COMPOSITIONS COMPRISING A PHOSPHONIC COMPOUND, AND ACIDS AS METHODS FOR PLANT GROWTH AND REGULATORY EFFECTS

(75) Inventor: Scott K Parrish, Spokane, WA (US)

(73) Assignee: AgQuam LLC, Spokane, WA (US)

( * ) Notice: Subject to any disclaimer, the term of this patent is extended or adjusted under 35 U.S.C. 154(b) by 355 days.

(21) Appl. No.: 10/728,419

(22) Filed: Dec. 8, 2003

(65) Prior Publication Data

US 2005/0124494 A1 Jun. 9, 2005

(51) Int. Cl.
*A01N 57/18* (2006.01)
*A01N 57/20* (2006.01)

(52) U.S. Cl. ...................................... 504/165; 504/208

(58) Field of Classification Search .................. 504/123, 504/127, 142, 163, 165, 171, 175, 182, 187, 504/188, 208, 320

See application file for complete search history.

(56) References Cited

U.S. PATENT DOCUMENTS

| | | | |
|---|---|---|---|
| 3,879,188 A * | 4/1975 | Fritz et al. ..................... | 504/208 |
| 4,119,399 A | 10/1978 | Feinland et al. | |
| 4,331,572 A | 5/1982 | Tomasi et al. | |
| 4,840,660 A | 6/1989 | Kowite | |
| 5,116,401 A | 5/1992 | Young | |
| 5,389,598 A | 2/1995 | Berk et al. | |
| 5,541,149 A | 7/1996 | Atwater et al. | |
| 5,658,855 A | 8/1997 | Nalewaja et al. | |
| 5,683,958 A | 11/1997 | Berger et al. | |
| 5,877,112 A | 3/1999 | Roberts et al. | |
| 6,180,566 B1 | 1/2001 | Nielsen et al. | |
| 6,541,424 B2 | 4/2003 | Roberts et al. | |
| 6,803,345 B2 | 10/2004 | Herold et al. | |
| 6,906,004 B2 | 6/2005 | Parrish et al. | |
| 7,094,735 B2 | 8/2006 | Herold et al. | |
| 2002/0107149 A1 | 8/2002 | Volgas et al. | |
| 2002/0160916 A1 | 10/2002 | Volgas et al. | |
| 2003/0104947 A1 | 6/2003 | Woznica et al. | |
| 2003/0125211 A1 | 7/2003 | Woznica et al. | |
| 2003/0144147 A1 | 7/2003 | Herold et al. | |
| 2003/0148889 A1 | 8/2003 | Herold et al. | |
| 2003/0153461 A1 | 8/2003 | Parrish et al. | |
| 2003/0153462 A1 | 8/2003 | Herold et al. | |
| 2004/0097372 A1 | 5/2004 | Abraham et al. | |
| 2004/0127364 A1 | 7/2004 | Herold et al. | |
| 2004/0167032 A1 | 8/2004 | Volgas et al. | |
| 2005/0170967 A1 | 8/2005 | Parrish et al. | |
| 2006/0205601 A1 | 9/2006 | Herold et al. | |
| 2006/0270557 A1 | 11/2006 | Volgas et al. | |
| 2007/0037707 A1 * | 2/2007 | Volgas et al. .................. | 504/194 |

FOREIGN PATENT DOCUMENTS

| | | | |
|---|---|---|---|
| CN | 1252940 | * | 5/2000 |
| CN | 1302545 | * | 7/2001 |

OTHER PUBLICATIONS

WPIDS Abstract 1986-007470; abstracting DD 227304 A (1985).*
Derwent Abstract 1997-133542; abstracting CN 1038382 C (1998).*
Farm Chemicals Handbook '98, Meister Publishing Co., Willoughby, Ohio, 1998, p. C 164.*
HCAPLUS abstract 2000:843249 (Dec. 2000).*
CABA abstract 80:49077 (Nov. 1994).*
The Agrochemicals Handbook, Unwin Brothers Ltd., Old Working (Surrey), United Kingdom, pp. A179, A180, the entry for "ethephon," Oct. 1983.*
Ethephon publication, EPA Pesticide Fact Sheet [online], Sep. 1988. Retrieved from the Internet on Nov. 19, 2008:< URL: http://pmep.cce.cornell.edu/profiles/herb-growthreg/dalapon-ethephon/etheph_prf_0988.html>.*
Imidacloprid publication, NY State Dept. of Environmental Conservation [online], Mar. 1995. Retrieved from the Internet on Nov. 19, 2008:< URL: http://pmep.cce.cornell.edu/profiles/insect-mite/fenitrothion-methylpara/imidacloprid/imidac_let_0395.html>.*
Florel Fruit Eliminator product literature, obtained online on May 13, 2011, publication date not available, <www.jlgardencenter.com/uploads/handouts/Florel%20Fruit%20Eliminator.pdf>.*
Gwathmey and Hayes, Harvest-Aid Interactions under Different Temperature Regimes in Field-Grown Cotton (1997) Journal of Cotton Science, 1:1-9.
2003 Cotton Defoliation/Harvest Aid Suggestions, Steven M. Brown, et al.
2006 Cotton Defoliation and Harvest Aid guide D.L. Wright and B. J. Brecke, University of Florida, Institute of Food and Agricultural Sciences.
Bohn et al. (1985) "Salt-Affected Soils, 8.6 Reclamation" Soil Chemistry, 2nd Ed, Wiley Interscience pp. 241-243.
Cox Glyphosate Factsheet, Journal of Pesticide Reform 2000, 108(3) part 1 and part 2.
Green et al. (1993) "Surfactant Structure and Concentration Strongly Affect Rimsulfuron Activity", Weed Technology 7:633-640.
Greenhouse Product News (Feb. 1999) "Water Chemistry as it Applies to pH and Alkalinity".
Hartzler (2001) "Role of AMS with Glyphosate Products", R. Extension Bulletin, Iowa State University.
Nalewaja and Matysiak (1993) "Influence of Diammonium Sulfate and Other Salts on Glyphosate Phytotoxicity", Pesticide Sci. 38:77-84.
Office Action mailed May 16, 2006 with respect to U.S. Appl. No. 10/853,781.
Office Action mailed Mar. 6, 2007 with respect to U.S. Appl. No. 10/853,781.
Office Action Final mailed Jul. 27, 2007 with respect to U.S. Appl. No. 10/853,781.
Office Action mailed Apr. 15, 2008 with respect to U.S. Appl. No. 10/853,781.
Office Action Final mailed Jan. 21, 2009 with respect to U.S. Appl. No. 10/853,781.
Office Action mailed Sep. 24, 2009 with respect to U.S. Appl. No. 10/853,781.

(Continued)

Primary Examiner — John Pak
(74) Attorney, Agent, or Firm — Swanson & Bratschun, L.L.C.

(57) ABSTRACT

It has been shown that the formulation of phosphonic compound (ethephon) with sulfuric acid increases the efficacy and efficiency of ethephon and the speed of the effect of the ethephon. It was theorized that the effect that is shown by the mixture of ethephon and sulfuric acid could be achieved using another acid. The effect was demonstrated using muratic acid. All acids that reduce the pH of the spray carrier are claimed in this patent as synergist for phosphonic acid compounds such as ethephon.

5 Claims, No Drawings

OTHER PUBLICATIONS

Office Action mailed Oct. 30, 2007 with respect to U.S. Appl. No. 10/997,634.

Office Action Final mailed Jul. 9, 2008 with respect to U.S. Appl. No. 10/997,634.

Office Action mailed Dec. 30, 2008 with respect to U.S. Appl. No. 10/997,634.

Office Action Final mailed Aug. 20, 2009 with respect to U.S. Appl. No. 10/997,634.

Petroff R., Water Effects on Pesticide Performance Apr. 12, 2003 (online) Retrieved from the internet < URL: http://web.archive.org/web/20030412083321/http://www.co.fergus.mt.us/weed/Water+Effects+on+Pesticide+Efficacy.html.>.

Petroff (2000) "Water Quality and Pesticide Performance", Pesticide Education Specialist, Montana State University Extension Service.

Reed (1996) "Water Quality Management for Greenhouse Production", Ball Publishing, Batavia, IL, ISBN: 1-883052-12-2.

The American Heritage Dictionary 1982 "include" 3 pages.

Thelen et al. (1995) "The Basis for the Hard-Water Antagonism of Glyphosate Activity", Weed Science 43(4):541-548.

* cited by examiner

COMPOSITIONS COMPRISING A PHOSPHONIC COMPOUND, AND ACIDS AS METHODS FOR PLANT GROWTH AND REGULATORY EFFECTS

CROSS-REFERENCE TO RELATED APPLICATIONS

| Atwater; Mark L. | Jul. 30, 1996 | 5,541,149 |
| Kowite, et al. | Jun. 20, 1989 | 4,840,660 |

1) JOURNAL OF COTTON SCIENCE, Volume 1, Issue 1, 1997 Page: 9

2) 2003 COTTON DEFOLIATION/HARVEST AID SUGGESTIONS Steven M. Brown, Extension Agronomist-Cotton, Philip H. Jost, Extension Agronomist-Cotton & Ag Crops, A. Stanley Culpepper, Extension Agronomist-Weed Science 3) 2002 Cotton Defoliation and Harvest Aid Guide D. L. Wright and B. J. Brecke, University of Florida, Institute of Food and Agricultural Sciences

BACKGROUND OF THE INVENTION

Phosphonic compounds (ethephon) have been used for years as plant growth regulators, harvest aids and defoliation products. Atwater et.al has shown that when ethephon is formulated in sulfuric acid and adduct the Plant Growth Regulated (PGR) effects are increased. The present invention shows that the increased in the PGR effect shown by Atwater occurs with other acids as well as with the sulfuric acid combinations claimed in the Atwater patent(s).

SUMMARY OF THE INVENTION

There is a need for increasing the defoliation and/or growth inhibition efficacy of phosphonic acid analog (ethephon). The present invention addresses this need by providing a composition formed by mixing ethephon and an acid in the same formulated agri-chemical product. This type of composition has significantly increased defoliation and growth inhibition efficacy as compared to ethephon applied alone. In addition to or in place of ethephon the composition optionally comprises one or more other phosphonic acids, phosphonic acid derivatives, or salts thereof. Any of several acids that lower the pH of the spray solution to a pH of between pH 2 and pH 4 will produce the effect.

DETAILED DESCRIPTION OF THE INVENTION

The phosphonic acids, phosphonic acid derivatives, and their salts (hereinafter collectively referred to as "phosphonic compounds"). Phosphonic compounds such as ethephon ($ClCH_2CH_2PO_3H_2$) or any phosphonic acid derivatives that will break down into ethylene in or on an plant when applied to the foliage of a target plant. These effects are increased and the speed of development is faster when the phposphonic compound is formulated in any acid that will buffer the application solution (water carrier) to a pH between 4 and 1. The spray solution should be applied in agricultural or horticultural application to the foliage of the target plant.

Specific acids employed in the present invention include, but are not limited to: hydrochloric, muratic, nitric, phosphoric, phosphorous, poly-phosphoric, perchloric, citric and acetic acids.

Specific phosphonic acids and phosphonic acid derivatives employed in the present invention include, but are not limited to:

1. The bis(acid chloride) of (2-chloroethyl)phosphonic acid.
2. The pyrocatechol cyclic ester of (2-chloroethyl)phosphonic acid.
3. The 4-chloropyrocatechol cyclic ester of (2-chloroethyl)phosphonic acid.
4. The mixed ethyl and 2-hydroxyphenyl diester of (2-chloroethyl)phosphonic acid.
5. The mixed butyl and 2-hydroxyphenyl diester of (2-chloroethyl)phosphonic acid.
6. The mixed propynyl and 2-hydroxyphenyl diester of (2-chloroethyl)phosphonic acid.
7. The 2-chloroethyl monoester of (2-chloroethyl)phosphonic acid.
8. (2-bromoethyl)phosphonic acid.
9. The bis(phenyl)ester of (2-chloroethyl)phosphonic acid.
10. The tetrachloropyrocatechol cyclic ester of (2-chloroethyl)phosphonic acid.
11. (2-iodoethyl)phosphonic acid.
12. The saligen cyclic ester of (2-chloroethyl)phosphonic acid.
13. The salicyclic acid cyclic ester of (2-chloroethyl)phosphonic acid.
14. (Phosphonoethyl)phosphonic acid.
15. (Phosphonoethylthioethyl)phosphonic acid.
16. The 3-hydroxyphenyl monoester of (2-chloroethyl)phosphonic acid (which exists in polymeric form).
17. The bis(2-oxo-pyrrolidinylmethyl)ester of (2-chloroethyl)phosphonic acid.
18. The o-hydroxyphenyl monoester of (2-chloroethyl)phosphonic acid.
19. The mixed isopropyl and 2-hydroxyphenyl diester of (2-chloroethyl)phosphonic acid.
20. (2-fluoroethyl)phosphonic acid.
21. The mixed octyl and 2-hydroxyphenyl diester of (2-chloroethyl)phosphonic acid.
22. The mixed hexadecyl and 2-hydroxyphenyl diester of (2-chloroethyl)phosphonic acid.
23. The mixed tridecyl and 2-hydroxyphenyl diester of (2-chloroethyl)phosphonic acid.
24. The anhydride of (2-chloroethyl)phosphonic acid.
25. (2-chloroethyl)phosphonic acid.
26. The 2-chloroethyl-butylester, 2-hydroxyphenylester of phosphonic acid.
27. The 2-chloroethyl-2-chloroethylester of phosphonic acid.
28. The salicyclic acid cyclic ester of phosphonoamidic acid.
29. The mixed phenyl and 2-hydroxyphenyl diester of (2-chloroethyl)phosphonic acid.
30. 2-chloroethyl-dichlorophosphine.
31. The bis(pentachlorophenyl)ester of (2-chloroethyl)phosphonic acid.
32. (2-chloropropyl)phosphonic acid.

33. (2-phenylthioethyl)phosphonic acid.
34. The 2,3-pyridinedio cyclic ester of (2-chloroethyl)phosphonic acid.
35. (2-chloroethyl)thiophosphonic acid.
36. 2-chloroethyl-2,3-dibromo-4-hydroxy-2-butyenyl ester polymer.

Salts of the foregoing phosphonic acids are optionally employed in the present invention. Exemplary salts include, but are not limited to, the salts of alkali metals, alkaline earth metals, aluminum, ammonium, and zinc. The preferred alkali metals are lithium, sodium, and potassium, and the preferred alkaline earth metals are calcium and magnesium.

The combination of the present invention is used advantageously to control vegetation. The efficacy for growth control depends, among other things, on the amount of the combination applied per hectare (acre) (A), the relative proportions of acid to the phosphonic compound, the treatment time, and the type of plant to which it is applied. The defoliation and growth inhibition effects exhibited by the combination are significantly better than those observed when the phosphonic compound is employed alone.

The combination of the present invention is used as a plant growth regulator on vegetation, including but not limited to, apples, barley, blackberries, bromeliads, cantaloupes, cherries, coffee, cotton, cranberries, cucumbers, figs, filberts, grapes, guava, lemons, Macadamia nuts, ornamentals, peppers, pineapples, rye, squash, tangerines, tangerine hybrids, tobacco, tomatoes, walnuts, wheat, rape, corn, flax, maize, oranges, peaches, rubber, and sugarcane.

While the combination of the present invention can be used alone, it generally is applied to plants in conjunction with other substances water carrier which will usually include; wetting agents, emulsifiers, solvents and other surface active agents.

Typical surface active agents which may be utilized include calcium-lignin sulfonate, polyoxyethyleneoctylphenol ether and naphthalene-sulfonic acids and their salts, phenolsulfonic acids and their salts, formaldehyde condensates, fatty alcohol sulfates, and substituted benzenesulfonic acids and their salts.

A preferred mixture would be 2-chlorophosphonic acid 10%-20% and Phosphoric Acid 1%-40%. This formulation would then be mixed with water as a carrier and applied to the foliage of the target plant at a rate of 3 gallons/Acre to 30 gallons/Acre. However, other acids will have a similar effect as seen in Table 1. Muratic Acid increased the efficacy of ethephon and the speed of the effect on cotton defoliation.

TABLE 1

Efficacy of ethephon applied with and with out the addition of muratic acid on the defoliation of cotton. Trial conducted in Bells TN October 2003.

| Trt-Eval Interval Trt No. | Target Code Part Rated Type Rating Unit Rating Date Treatment Name | Rate | Rate Unit | Cotton LEAF DEFOLIATION percent Oct. 13, 2003 3 DA-A | | Cotton LEAF DEFOLIATION percent Oct. 16, 2003 6 DA-A | |
|---|---|---|---|---|---|---|---|
| 1 | Untreated | | | 0 | b | 0 | c |
| 2 | ETHEPHON | 16 | FL OZ/A | 10.8 | b | 19.6 | bc |
| 3 | ETHEPHON MURATIC ACID | 16 4 | FL OZ/A % V/V | 16.7 | a | 30 | b |
| 4 | ETHEPHON | 32 | FL OZ/A | 16.7 | b | 16.7 | bc |
| 5 | ETHEPHON MURATIC ACID | 32 4 | FL OZ/A % V/V | 30 | a | 46.7 | a |

The invention claimed is:

1. A method for increasing the efficiency and efficacy of phosphonic compounds in controlling cotton plant defoliation and boll opening, the method comprising the steps of:
   (a) preparing a concentrate composition consisting essentially of a mixture of
      (i) 1% to 40% phosphoric acid;
      (ii) 10% to 20% of one or more phosphonic compounds, wherein said phosphonic compound is selected from the group consisting of 2-chloroethyl)phosphonic acid and salts of (2-chloroethyl)phosphonic acid; and
      (iii) one or more surface active agent selected from the group consisting of calcium lignin sulfonate, polyoxyethyleneoctylphenol ether, naphthalene sulfonic acids, naphthalene sulfonic acid salts, fatty alcohol sulfates, substituted benzenesulfonic acids, and substituted benzenesulfonic acid salts;
   wherein the phosphoric acid is present in sufficient amount to buffer a diluted application solution of said concentrate composition to a pH between 2 and 4;
   (b) mixing said concentrate composition of step (a) with water to form an application solution, wherein the application solution has a buffered pH between 2 and 4; and
   (c) applying said application solution formed in step (b) to a cotton plant in an amount effective to increase the efficiency and efficacy of the one or more phosphonic compounds in controlling cotton plant defoliation and boll opening.

2. The method of claim 1, wherein the boll opening efficiency of the compound is increased.

3. The method of claim 1, wherein the defoliation efficiency of the compound is increased.

4. The method of claim 1, wherein the rate of application is 3 to 30 gallons per acre.

5. The method of claim 1, wherein the application solution formed in step (b) further includes one or more ingredients selected from the group consisting of a wetting agent, an emulsifier, a solvent and a surface active agent.

* * * * *